US011234706B2

(12) United States Patent
Inouye

(10) Patent No.: US 11,234,706 B2
(45) Date of Patent: Feb. 1, 2022

(54) OCCLUSIVE MEDICAL DEVICE

(71) Applicant: BOSTON SCIENTIFIC SCIMED, INC., Maple Grove, MN (US)

(72) Inventor: Joshua Mark Inouye, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 90 days.

(21) Appl. No.: 16/276,141

(22) Filed: Feb. 14, 2019

(65) Prior Publication Data

US 2019/0247053 A1    Aug. 15, 2019

Related U.S. Application Data

(60) Provisional application No. 62/630,805, filed on Feb. 14, 2018.

(51) Int. Cl.
*A61B 17/12*    (2006.01)

(52) U.S. Cl.
CPC ........ *A61B 17/12145* (2013.01); *A61B 17/12* (2013.01); *A61B 17/1215* (2013.01);
(Continued)

(58) Field of Classification Search
CPC .............. A61B 17/12; A61B 17/12145; A61B 17/12031; A61B 17/12122;
(Continued)

(56) References Cited

U.S. PATENT DOCUMENTS

| 5,375,612 A | 12/1994 | Cottenceau et al. |
| 5,509,899 A | 4/1996 | Fan et al. |

(Continued)

FOREIGN PATENT DOCUMENTS

| CN | 1638703 A | 7/2005 |
| CN | 101185582 A | 5/2008 |

(Continued)

OTHER PUBLICATIONS

Khattab, et al; "Transcatheter Devices for Left Atrial Appendage Occlusion," Cardiovascular Medicine, 13(4), 130-134, 2010.
(Continued)

*Primary Examiner* — Kathleen S Holwerda
*Assistant Examiner* — Uyen N Vo
(74) *Attorney, Agent, or Firm* — Seager, Tufte & Wickhem LLP

(57) ABSTRACT

An example occlusive implant is disclosed. The example occlusive implant includes an expandable framework including a height and a plurality of support members defining a proximal end region of the expandable framework and a central hub member attached to the plurality of support members. Additionally, the expandable framework is configured to shift between a first configuration and a second configuration, wherein the height of the expandable framework remains substantially the same in both the first configuration and the second configuration. Further, the central hub member is configured to shift relative to the proximal end region while the expandable framework shifts between the first configuration and the second configuration.

15 Claims, 13 Drawing Sheets

(52) U.S. Cl.
CPC .. *A61B 17/12031* (2013.01); *A61B 17/12122* (2013.01); *A61B 17/12172* (2013.01); *A61B 2017/1205* (2013.01)

(58) Field of Classification Search
CPC .......... A61B 17/1215; A61B 17/12172; A61B 17/0057; A61B 17/12177; A61B 17/12022; A61B 17/122; A61B 2017/1205; A61B 2017/00243; A61B 2017/00575; A61B 2017/12095; A61B 2017/00601; A61B 2017/00603; A61B 2017/12054; A61B 2017/00867; A61B 17/12113; A61B 17/12114; A61B 17/12168; A61B 17/00632; A61B 2017/00597; A61F 2/01; A61F 2/011; A61F 2002/018
See application file for complete search history.

(56) References Cited

U.S. PATENT DOCUMENTS

| | | | |
|---|---|---|---|
| 5,814,064 A * | 9/1998 | Daniel et al. | 606/200 |
| 6,152,144 A | 11/2000 | Lesh et al. | |
| 6,231,561 B1 | 5/2001 | Frazier et al. | |
| 6,290,674 B1 | 9/2001 | Roue et al. | |
| 6,328,727 B1 | 12/2001 | Frazier et al. | |
| 6,419,669 B1 | 7/2002 | Frazier et al. | |
| 6,436,088 B2 | 8/2002 | Frazier et al. | |
| 6,458,100 B2 | 10/2002 | Roue et al. | |
| 6,537,300 B2 | 3/2003 | Girton | |
| 6,551,303 B1 | 4/2003 | Van Tassel et al. | |
| 6,561,969 B2 | 7/2003 | Schaer | |
| 6,595,989 B1 | 7/2003 | Schaer | |
| 6,641,557 B1 | 11/2003 | Frazier et al. | |
| 6,652,555 B1 | 11/2003 | Van Tassel et al. | |
| 6,652,556 B1 | 11/2003 | Van Tassel et al. | |
| 6,673,053 B2 | 1/2004 | Wang et al. | |
| 6,689,150 B1 | 2/2004 | Van Tassel et al. | |
| 6,702,825 B2 | 3/2004 | Frazier et al. | |
| 6,712,804 B2 | 3/2004 | Roue et al. | |
| 6,730,108 B2 | 5/2004 | Van Tassel et al. | |
| 6,730,119 B1 | 5/2004 | Smalling | |
| 6,746,472 B2 | 6/2004 | Frazier et al. | |
| 6,949,113 B2 | 9/2005 | Van Tassel et al. | |
| 6,994,092 B2 | 2/2006 | van der Burg et al. | |
| 7,011,671 B2 | 3/2006 | Welch | |
| 7,025,756 B2 | 4/2006 | Frazier et al. | |
| 7,044,134 B2 | 5/2006 | Khairkhahan et al. | |
| 7,115,110 B2 | 10/2006 | Frazier et al. | |
| 7,128,073 B1 | 10/2006 | van der Burg et al. | |
| 7,152,605 B2 | 12/2006 | Khairkhahan | |
| 7,169,164 B2 | 1/2007 | Borillo et al. | |
| 7,192,439 B2 | 3/2007 | Khairkhahan et al. | |
| 7,338,514 B2 | 3/2008 | Wahr et al. | |
| 7,427,279 B2 | 9/2008 | Frazier et al. | |
| 7,544,381 B2 | 6/2009 | Kangas | |
| 7,549,983 B2 | 6/2009 | Roue et al. | |
| 7,566,336 B2 | 7/2009 | Corcoran et al. | |
| 7,597,704 B2 | 10/2009 | Frazier et al. | |
| 7,674,256 B2 | 3/2010 | Marrouche et al. | |
| 7,713,282 B2 | 5/2010 | Frazier et al. | |
| 7,722,641 B2 | 5/2010 | van der Burg et al. | |
| 7,727,189 B2 | 6/2010 | Van Tassel et al. | |
| 7,735,493 B2 | 6/2010 | van der Burg et al. | |
| 7,780,683 B2 | 8/2010 | Roue et al. | |
| 7,914,809 B2 | 3/2011 | Atanasoka et al. | |
| 7,972,359 B2 | 7/2011 | Kreidler | |
| 8,034,061 B2 | 10/2011 | Amplatz et al. | |
| 8,043,305 B2 | 10/2011 | Frazier et al. | |
| 8,043,329 B2 | 10/2011 | Khairkhahan et al. | |
| 8,048,060 B2 | 11/2011 | Griffin et al. | |
| 8,052,715 B2 | 11/2011 | Quinn et al. | |
| 8,080,032 B2 | 12/2011 | van der Burg et al. | |
| 8,197,496 B2 | 6/2012 | Roue et al. | |
| 8,197,527 B2 | 6/2012 | Borillo et al. | |
| 8,221,384 B2 | 7/2012 | Frazier et al. | |
| 8,221,445 B2 | 7/2012 | van Tassel et al. | |
| 8,282,668 B2 * | 10/2012 | McGuckin et al. | 606/200 |
| 8,287,563 B2 | 10/2012 | Khairkhahan et al. | |
| 8,313,505 B2 | 11/2012 | Amplatz et al. | |
| 8,323,309 B2 | 12/2012 | Khairkhahan et al. | |
| 8,398,670 B2 | 3/2013 | Amplatz et al. | |
| 8,454,633 B2 | 6/2013 | Amplatz et al. | |
| 8,523,897 B2 | 9/2013 | van der Burg et al. | |
| 8,535,343 B2 | 9/2013 | van der Burg et al. | |
| 9,883,936 B2 | 2/2018 | Sutton et al. | |
| 2001/0000797 A1 | 5/2001 | Mazzocchi | |
| 2001/0039434 A1 | 11/2001 | Frazier et al. | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0049492 A1 | 12/2001 | Frazier et al. | |
| 2002/0111647 A1 | 8/2002 | Khairkhahan et al. | |
| 2003/0023266 A1 | 1/2003 | Borillo | |
| 2003/0181942 A1 * | 9/2003 | Sutton | A61B 17/0057 606/200 |
| 2003/0195555 A1 | 10/2003 | Khairkhahan et al. | |
| 2003/0199923 A1 | 10/2003 | Khairkhahan et al. | |
| 2003/0204203 A1 | 10/2003 | Khairkhahan et al. | |
| 2003/0212432 A1 | 11/2003 | Khairkhahan et al. | |
| 2003/0220667 A1 | 11/2003 | van der Burg et al. | |
| 2004/0034366 A1 | 2/2004 | van der Burg et al. | |
| 2004/0044361 A1 | 3/2004 | Frazier et al. | |
| 2004/0098031 A1 | 5/2004 | van der Burg et al. | |
| 2004/0111147 A1 | 6/2004 | Rabkin et al. | |
| 2004/0186486 A1 | 9/2004 | Roue et al. | |
| 2004/0215169 A1 | 10/2004 | Li | |
| 2004/0215230 A1 | 10/2004 | Frazier et al. | |
| 2004/0220595 A1 | 11/2004 | Frazier et al. | |
| 2004/0230222 A1 | 11/2004 | van der Burg et al. | |
| 2005/0004652 A1 | 1/2005 | van der Burg et al. | |
| 2005/0038470 A1 | 2/2005 | van der Burg et al. | |
| 2005/0070952 A1 | 3/2005 | Devellian | |
| 2005/0125032 A1 | 6/2005 | Whiseant et al. | |
| 2005/0149115 A1 | 7/2005 | Roue et al. | |
| 2005/0177182 A1 | 8/2005 | van der Burg et al. | |
| 2005/0192627 A1 | 9/2005 | Whisenant et al. | |
| 2005/0203568 A1 | 9/2005 | van der Burg et al. | |
| 2005/0234543 A1 | 10/2005 | Glaser et al. | |
| 2005/0283186 A1 | 12/2005 | Barrada et al. | |
| 2006/0184234 A1 | 8/2006 | Frazier et al. | |
| 2006/0206148 A1 | 9/2006 | Khairkhahan et al. | |
| 2007/0066993 A1 | 3/2007 | Kreidler | |
| 2007/0066994 A1 | 3/2007 | Blaeser et al. | |
| 2007/0080188 A1 | 4/2007 | Spence et al. | |
| 2007/0083227 A1 | 4/2007 | van der Burg et al. | |
| 2007/0112380 A1 | 5/2007 | Figulla et al. | |
| 2007/0129753 A1 | 6/2007 | Quinn et al. | |
| 2007/0135826 A1 | 6/2007 | Zaver et al. | |
| 2007/0162048 A1 | 7/2007 | Quinn et al. | |
| 2008/0071350 A1 | 3/2008 | Stinson | |
| 2008/0071358 A1 | 3/2008 | Weber et al. | |
| 2009/0028785 A1 | 1/2009 | Clarke | |
| 2009/0098176 A1 | 4/2009 | Helmus et al. | |
| 2009/0099647 A1 | 4/2009 | Glimsdale et al. | |
| 2010/0069838 A1 | 3/2010 | Weber et al. | |
| 2010/0087783 A1 | 4/2010 | Weber et al. | |
| 2010/0228281 A1 | 9/2010 | Gilson et al. | |
| 2011/0022149 A1 | 1/2011 | Cox et al. | |
| 2011/0054515 A1 * | 3/2011 | Bridgeman | A61B 17/0057 606/200 |
| 2011/0218566 A1 | 9/2011 | van der Burg et al. | |
| 2011/0301630 A1 | 12/2011 | Hendriksen et al. | |
| 2011/0319917 A1 | 12/2011 | Ferrera et al. | |
| 2012/0029541 A1 | 2/2012 | Frazier et al. | |
| 2012/0029553 A1 | 2/2012 | Quinn et al. | |
| 2012/0035643 A1 | 2/2012 | Khairkhahan et al. | |
| 2012/0065662 A1 | 3/2012 | van der Burg et al. | |
| 2012/0095396 A1 | 4/2012 | Radhakrishnan | |
| 2012/0232585 A1 | 9/2012 | Roue et al. | |
| 2012/0239077 A1 | 9/2012 | Zaver et al. | |
| 2012/0239083 A1 | 9/2012 | Kreidler | |

(56) References Cited

U.S. PATENT DOCUMENTS

| | | | |
|---|---|---|---|
| 2013/0012982 A1 | 1/2013 | Khairkhahan et al. | |
| 2013/0110154 A1 | 5/2013 | van der Burg et al. | |
| 2013/0138138 A1* | 5/2013 | Clark | A61B 17/12177 606/200 |
| 2014/0018841 A1 | 1/2014 | Peiffer et al. | |
| 2014/0074151 A1* | 3/2014 | Tischler | A61B 17/12122 606/200 |
| 2014/0135817 A1 | 5/2014 | Tischler et al. | |
| 2015/0196300 A1* | 7/2015 | Tischler | A61B 17/12122 606/191 |
| 2016/0051358 A1 | 2/2016 | Sutton et al. | |
| 2016/0287261 A1* | 10/2016 | Li | A61B 17/12172 |
| 2017/0156898 A1* | 6/2017 | Obradovic | A61B 17/12172 |

FOREIGN PATENT DOCUMENTS

| | | |
|---|---|---|
| CN | 202335893 U | 7/2012 |
| DE | 102005053958 A1 | 5/2007 |
| DE | 102008015781 A1 | 10/2009 |
| EP | 1223890 B1 | 4/2004 |
| EP | 1227770 B1 | 9/2004 |
| EP | 1923019 A1 | 5/2008 |
| EP | 1616530 A1 | 10/2008 |
| EP | 2074953 A1 | 1/2009 |
| EP | 1659988 B1 | 2/2010 |
| EP | 1620020 B1 | 9/2010 |
| EP | 1135068 B1 | 6/2011 |
| EP | 1441649 B1 | 8/2011 |
| EP | 3073936 A1 | 10/2016 |
| ES | 2353827 T3 | 3/2011 |
| JP | 2003529384 A | 10/2003 |
| JP | 2005515830 A | 6/2005 |
| JP | 2009160402 A | 7/2009 |
| WO | 9912478 A1 | 3/1999 |
| WO | 0027292 A1 | 5/2000 |
| WO | 0130267 A1 | 5/2001 |
| WO | 0130268 A1 | 5/2001 |
| WO | 02071977 A2 | 9/2002 |
| WO | 03007825 A1 | 1/2003 |
| WO | 03063732 A2 | 8/2003 |
| WO | 03063732 A3 | 8/2003 |
| WO | 2004096060 A2 | 11/2004 |
| WO | 2007054116 A1 | 5/2007 |
| WO | 2007140797 A1 | 12/2007 |
| WO | 2008125689 A1 | 10/2008 |
| WO | 2008151204 A1 | 12/2008 |
| WO | 2009091425 A1 | 7/2009 |
| WO | 2011147783 A1 | 12/2011 |
| WO | 2013071115 A1 | 5/2013 |

OTHER PUBLICATIONS

AMPLATZER—Registered Trademark—Vascular Plug Family, http://web.archive.org/web/20100514232852/http://international amplatzer.com/InternationalProducts/VascularPlugFamily/tabid/528/Default.aspx,accessed Oct. 9, 2013, and said, by the Wayback Machine, to have been archived on May 14, 2010.

AMPLATZER—Registered Trademark—Cardiac Plug, http: //web.archive.org/web/20090809150223/http://internationalamplatzer.com/International_Products/ Cardiac Plug/tabid/815/Default.aspx,accessed Oct. 9, 2013, and said, by the Wayback Machine, to have been archived on Aug. 9, 2009.

Notification of Transmittal of the International Search Report and Written Opinion of the International Searching Authority, or the Declaration for PCT/US2013/050060, dated Oct. 15, 2013.

Dictionary.com definition of "within" accessed on Sep. 13, 2017.

Invitation to Pay Additional Fees dated Jun. 5, 2019 for International Application No. PCT/US2019/018034.

\* cited by examiner

OCCLUSIVE MEDICAL DEVICE

CROSS-REFERENCE TO RELATED APPLICATIONS

This application claims the benefit of priority under 35 U.S.C. § 119 to U.S. Provisional Application Ser. No. 62/630,805, filed Feb. 14, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

This disclosure provides design, material, manufacturing method, and use alternatives for medical devices. An example occlusive implant includes an expandable framework including a height and a plurality of support members defining a proximal end region of the expandable framework and a central hub member attached to the plurality of support members. Additionally, the expandable framework is configured to shift between a first configuration and a second configuration, wherein the height of the expandable framework remains substantially the same in both the first configuration and the second configuration. Further, the central hub member is configured to shift relative to the proximal end region while the expandable framework shifts between the first configuration and the second configuration.

In addition or alternatively, wherein the expandable framework includes a first radial outward force in the first configuration and a second radial outward force in the second configuration, and wherein the first radial outward force is substantially equivalent to the second radial outward force.

In addition or alternatively, wherein the expandable framework includes a longitudinal axis, and wherein central hub member is configured to shift along the longitudinal axis.

In addition or alternatively, wherein the central hub member shifts in a distal direction when shifting from the first configuration to the second configuration.

In addition or alternatively, wherein the plurality of support members define a recess within a central region of the expandable framework.

In addition or alternatively, wherein the central hub member is positioned within the recess.

In addition or alternatively, wherein the expandable member has a first width in the first configuration and a second width in the second configuration, wherein the first width is wider than the second width.

In addition or alternatively, wherein the recess of the expandable member has a first recess height in the first configuration and a second recess height in the second configuration, and wherein the second recess height is greater than the first recess height.

In addition or alternatively, further comprising a first occlusive member disposed along the proximal end region of the expandable framework.

In addition or alternatively, further comprising a second occlusive member disposed along a distal end region of the expandable framework.

Another medical implant for occluding a left atrial appendage includes:

an expandable framework including a first height, a proximal end region and a plurality of support members defining a central recessed region; and a central hub member attached to the plurality of support members and positioned within the central recessed region;

wherein the central recess region extends into the expandable member a first distance;

wherein the expandable framework is configured to shift between an expanded configuration and a collapsed configuration;

wherein the first distance increases as the expandable framework shifts between the expanded configuration and the collapsed configuration.

In addition or alternatively, wherein the height of the expandable framework remains substantially the same in both the expanded configuration and the collapsed configuration.

In addition or alternatively, wherein the expandable framework includes a first radial outward force in the expanded configuration and a second radial outward force in the collapsed configuration, and wherein the first radial outward force is substantially equivalent to the second radial outward force.

In addition or alternatively, wherein the central hub member is configured to shift relative to the proximal end region while the expandable framework shifts between the expanded configuration and the collapsed configuration.

In addition or alternatively, wherein the expandable framework includes a longitudinal axis, and wherein the central hub member is configured to shift along the longitudinal axis.

In addition or alternatively, wherein the central hub member shifts in a distal direction when shifting from the expanded configuration to the collapsed configuration.

In addition or alternatively, further comprising a first occlusive member disposed along the proximal end region of the expandable framework.

In addition or alternatively, further comprising a second occlusive member disposed along a distal end region of the expandable framework.

An example method for occluding a left atrial appendage includes:

advancing an occlusive implant to the left atrial appendage, the occlusive implant including:

an expandable framework including a height and a plurality of support members defining a proximal end region of the expandable framework;
a central hub member attached to the plurality of support members;
wherein the expandable framework is configured to shift between a first configuration and a second configuration;
wherein the height of the expandable framework remains substantially the same in both the first configuration and the second configuration; and
expanding the expandable framework within the left atrial appendage such that the expandable framework shifts between the first configuration and the second configuration.

In addition or alternatively, wherein expanding that expandable framework from the first configuration to the second expanded configuration shifts the central hub member relative to the proximal end region The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
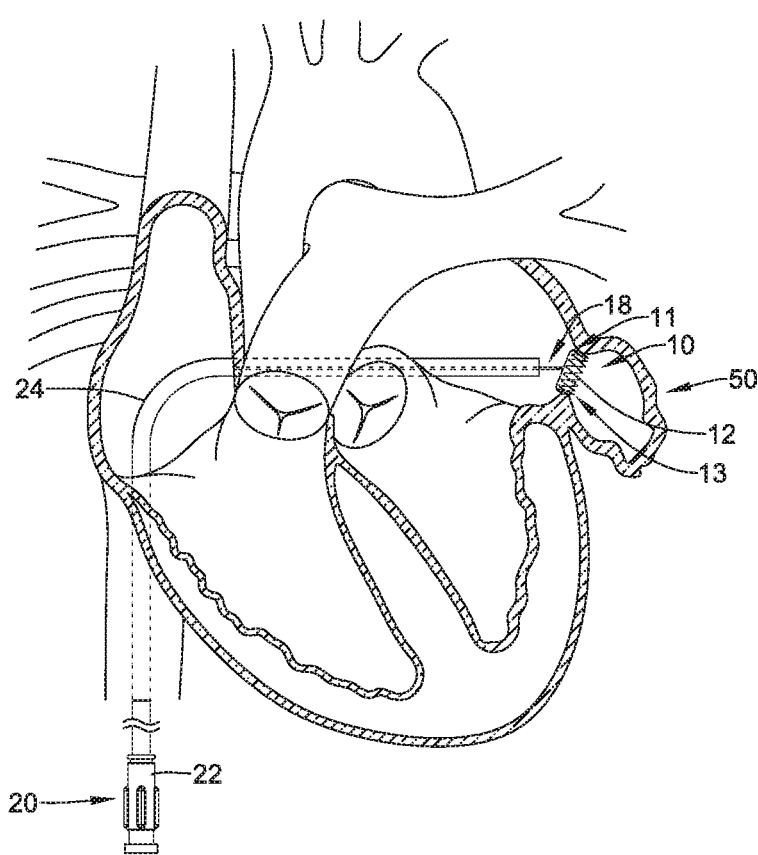
FIG. 1 illustrates an example occlusive implant positioned in the heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants which seal the left atrial appendage (or other similar openings) are disclosed herein.

FIG. 1 illustrates an example occlusive implant 10 positioned within the left atrial appendage 50. FIG. 1 further illustrates that the occlusive implant 10 may be inserted and advanced through a body lumen via an occlusive implant delivery system 20. In some instances, an occlusive implant delivery system 20 may include a delivery catheter 24 which is guided toward the left atrium via various chambers and lumens of the heart (e.g., the inferior vena cava, superior vena cava, the right atrium, etc.) to a position adjacent the left atrial appendage 50.

The delivery system 20 may include a hub 22. The hub 22 may be manipulated by a clinician to direct the distal end region of the delivery catheter 24 to a position adjacent the left atrial appendage 50. In some embodiments, an occlusive implant delivery system 20 may include a core wire 18. Further, a proximal end 11 of the occlusive implant 10 may be configured to releasably attach, join, couple, engage, or otherwise connect to the distal end of the core wire 18. In some embodiments, the proximal end region 11 of the occlusive implant 10 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the occlusive implant 10 to the distal end of the core wire 18 are also contemplated.

FIG. 1 further illustrates the occlusive implant 10 positioned adjacent the left atrial appendage 50 via the delivery catheter 24 (described above). It can be appreciated that in some examples, the implant 10 may be configured to shift between a collapsed configuration and an expanded configuration. For example, in some instances, the occlusive implant 10 may be in a collapsed configuration during delivery via the occlusion implant delivery system 20, whereby the occlusive implant 10 expands to an expanded configuration once deployed from the occlusion implant delivery system 20.

Additionally, FIG. 1 illustrates that the occlusive implant 10 may include an expandable framework 12. The expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue and/or lateral wall of the left atrial appendage 50. Further, it can be appreciated that the elements of the expandable framework 12 may be tailored to increase the flexibility of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 to include various features, components and/or configurations which improve the sealing capabilities of the occlusive implant 10 within the left atrial appendage.

FIG. 1 illustrates that the distal end region 13 of the expandable framework 12 may extend farther into the left atrial appendage 50 as compared to the proximal end region 11 of the expandable framework 12. It can be appreciated that as the expandable framework 12 is advanced into the left atrial appendage 50, the distal end region 13 may engage with tissue defining the left atrial appendage 50. In other words, in some examples the distal end region 13 may be considered the "leading" region of the expandable framework 12 as it enters into the left atrial appendage 50. However, this is not intended to be limiting. Rather, in some examples the proximal end region 11 may be considered the "leading" region of the expandable framework 12 as it enters into the left atrial appendage 50.

Figure 2:
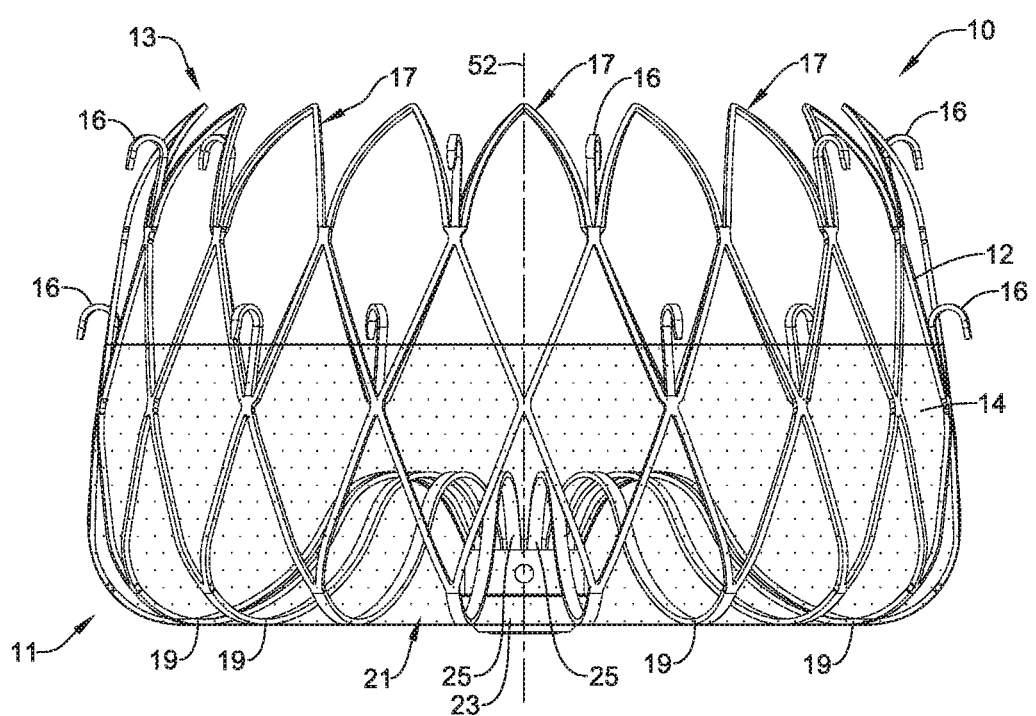
FIG. 2 is a plan view of an example occlusive implant.

FIG. 2 illustrates an example occlusive implant 10. The implant 10 may include an expandable framework 12. The expandable framework 12 may include a proximal end region 11 and a distal end region 13. FIG. 2 further illustrates that the expandable framework 12 may include one or more projections 17 extending in a proximal-to-distal direction. In some instances (such as that shown in FIG. 2), plurality of projections 17 may extend circumferentially around a longitudinal axis 52 of the expandable framework 12. In other words, in some examples the projections 17 may resemble the peaks of a "crown" extending circumferentially around a longitudinal axis 52 of the expandable framework 12. While the above discussion (and the illustration shown in FIG. 2), shows a plurality of projections 17, it is contemplated that the occlusive implant 10 may include 1, 2, 3, 4, 5, 6, 7, 8, 9, 10, 11, 12 or more individual projections 17 disposed in a variety of arrangements along the expandable framework 12.

Additionally, FIG. 2 illustrates that the proximal end region 11 of the expandable framework 12 may include a plurality of support members 19 extending circumferentially around the longitudinal axis 52 of the expandable framework 12. FIG. 2 illustrates that that plurality of support members 19 may include one or more curved portions which are shaped such that they define a "recess" 21 extending distally into the expandable framework 12. As illustrated in FIG. 2, the recess 21 may extend circumferentially around the longitudinal axis 52. Further, FIG. 2 illustrates that each of the plurality of support members 19 may include a first end 25 which is attached to a central hub 23. It can be appreciated that the central hub 23 may be aligned along the longitudinal axis 52 of the expandable framework 12. As will be described in greater detail below, FIG. 2 illustrates that the hub 23 may be positioned such that it lies within the recess 21 defined by the plurality of support members 19.

The occlusive implant 10 may also include a first occlusive member 14 disposed on, disposed over, disposed about, or covering at least a portion of the expandable framework 12. In some embodiments, the first occlusive member 14 may be disposed on, disposed over, disposed about or cover at least a portion of an outer (or outwardly-facing) surface of the expandable framework 12. FIG. 2 further illustrates that the first occlusive member 14 may extend only partially along the longitudinal extent of the expandable framework 12. However, this is not intended to be limiting. Rather, the first occlusive member 14 may extend along the longitudinal extent of the expandable framework 12 to any degree (e.g., the full longitudinal extend of the expandable framework 12).

In some embodiments, the first occlusive member 14 may be permeable or impermeable to blood and/or other fluids, such as water. In some embodiments, the first occlusive member 14 may include a woven, braided and/or knitted material, a fiber, a sheet-like material, a fabric, a polymeric membrane, a metallic or polymeric mesh, a porous filter-like material, or other suitable construction. In some embodiments, the first occlusive member 14 may prevent thrombi (i.e. blood clots, etc.) from passing through the first occlusive member 14 and out of the left atrial appendage into the blood stream. In some embodiments, the first occlusive member 14 may promote endothelialization after implantation, thereby effectively removing the left atrial appendage from the patient's circulatory system. Some suitable, but non-limiting, examples of materials for the first occlusive member 14 are discussed below.

FIG. 2 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 2. Some suitable, but non-limiting, examples of materials for the expandable framework 12 and/or the plurality of anchor members 16 are discussed below.

In some examples, the expandable framework 12 and the plurality of anchor members 16 may be integrally formed and/or cut from a unitary member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are al so contemplated.

As illustrated in FIG. 2, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

Figure 2A:
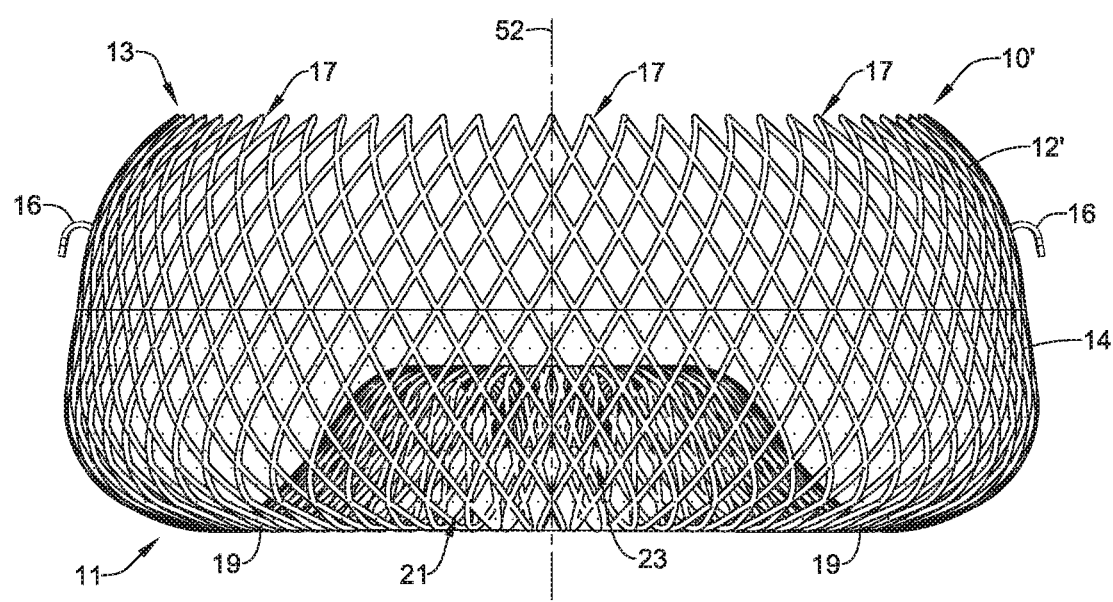
FIG. 2A is a plan view of another example occlusive implant.

While FIG. 2 illustrates an expandable framework 12 which may be formed from a unitary member, this is not intended to be limiting. Rather, it is contemplated the expandable member 12 may include a variety of different configurations which may be formed via a variety of manufacturing techniques. For example, FIG. 2A illustrates another example occlusive implant 10'. FIG. 2A further illustrates that the example occlusive implant 10' may include an expandable framework 12'. As illustrated in FIG. 2A, the expandable framework 12' may be formed as a braided structure (e.g., a framework formed by braiding one or more filaments together). Additionally, the expandable framework 12' may include one or more of the features described above with respect to FIG. 2.

Figure 3:
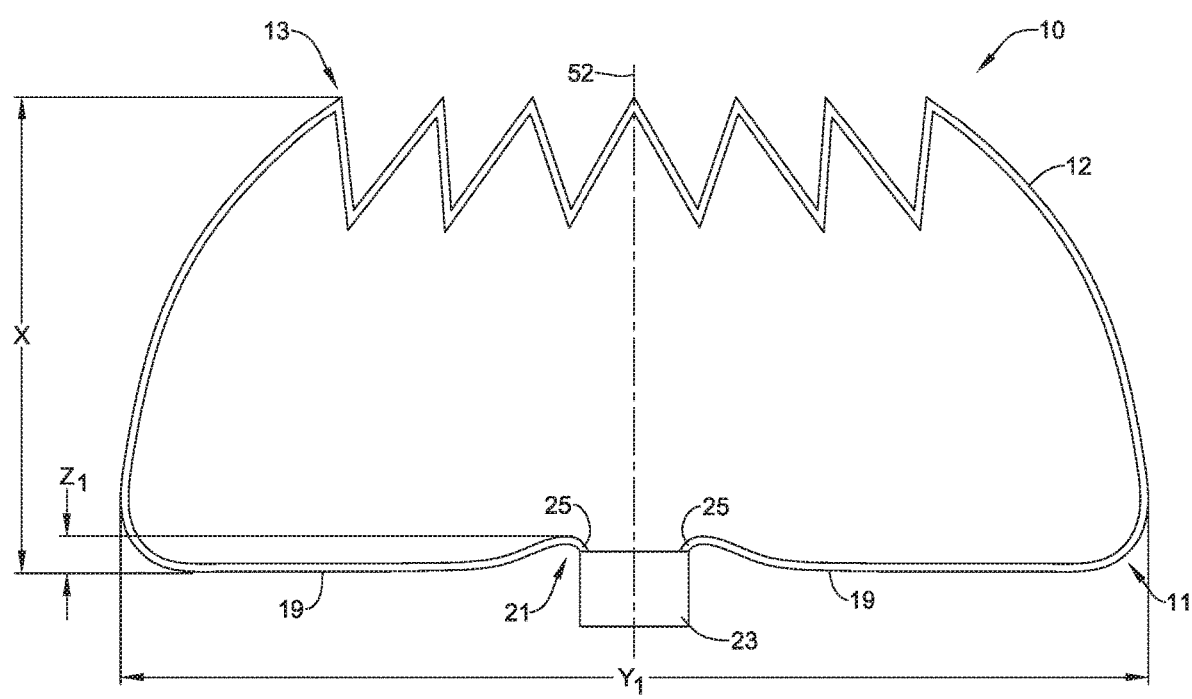
FIG. 3 is a plan view of another example occlusive implant.
Figure 4:
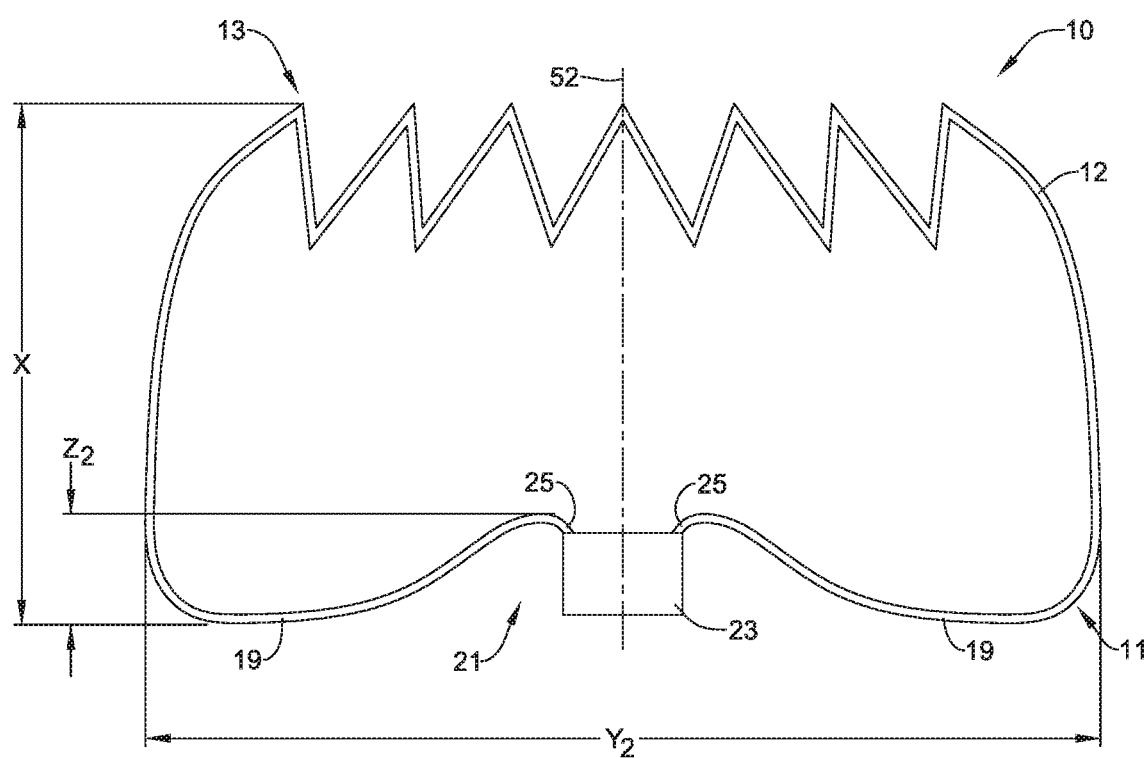
FIG. 4 is a plan view of another example occlusive implant.
Figure 5:
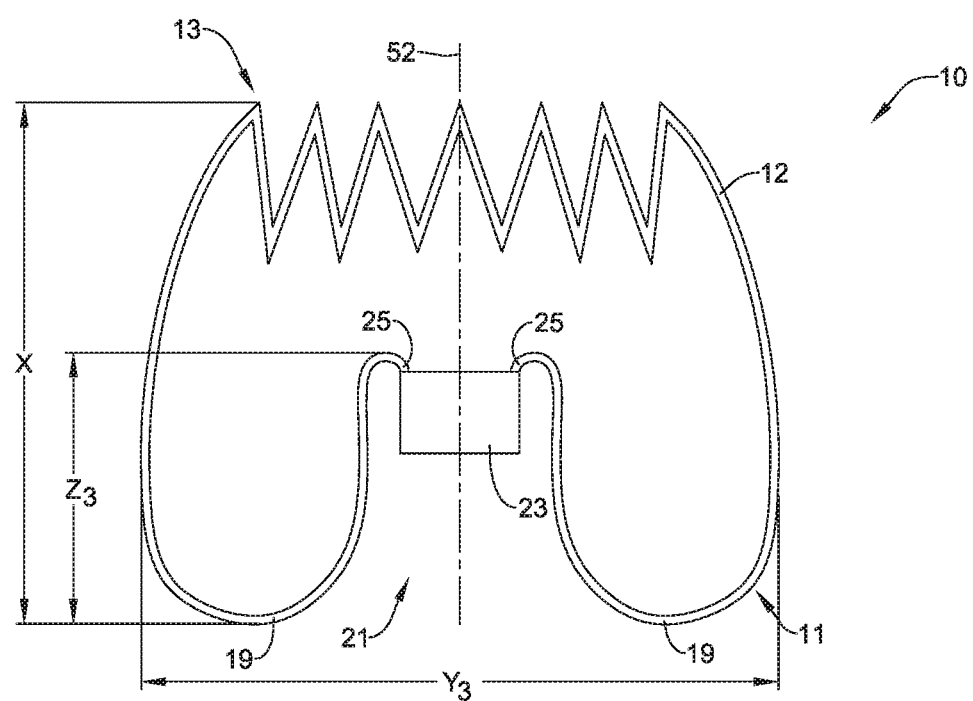
FIG. 5 is a plan view of another example occlusive implant.

As discussed above, it may be desirable to design the occlusive implant 10 described herein to include features which allow it to accommodate patient-to-patient variability in the shape of the left atrial appendage. In other words, it may be desirable to design the occlusive implant 10 such that a clinician may utilize the same device irrespective of the particular anatomy presented by a particular patient. For example, it is known that the diameter of the opening (e.g., orifice) of the left atrial appendage may vary widely among individuals. In particular, the diameter of the opening to the left atrial appendage may be narrower in certain individuals as compared to others. Therefore, it may be desirable to design the occlusive implant 10 such that it can change its shape to fit different orifice diameters of the left atrial appendage without sacrificing its effectiveness in sealing the left atrial appendage. In particular, it may be desirable to design the occlusive implant 10 such that it can expand or collapse its width without substantially changing the distance in which it extends into the left atrial appendage and without substantially changing the radial force in which it exerts upon the surrounding tissue. FIGS. 3-5 illustrate an example occlusive implant 10 which may expand or collapse its width without substantially changing the distance in which it extends into the left atrial appendage and without substantially changing the radial force in which the implant exerts upon surrounding tissue In the interest of simplicity, FIG. 3 illustrates a "silhouette" of the occlusive implant 10 (described above) in an expanded configuration. In particular, FIG. 3 illustrates an outline of the expandable framework 12 including a distal end region 13 and a proximal end region 11. Further, FIG. 3 illustrates two of the plurality of support members 19 of the expandable framework 12 described above. The support members 19 may be positioned adjacent to the proximal end region 11. Additionally, FIG. 3 illustrates the first ends 25 of each of the support members 19 attached to a central hub 23. The central hub 23 may be aligned with the longitudinal axis 52 of the occlusive member 10 and partially extend into a recess 21 defined by curved portions of the support members 19.

As discussed above, FIG. 3 illustrates the occlusive implant 10 in an expanded configuration (e.g., an expanded configuration as compared to the configuration of the implant 10 shown in FIG. 2, above). FIG. 3 illustrates that the expandable framework 12 may include a "height" defined as the distance between the proximal end region 11 and the distal end region 13. As shown in FIG. 3, the height of the expandable framework 12 is depicted as "X." As will be described in greater detail below, the height of the occlusive implant 10 may correspond to the distance in which the implant extends into a left atrial appendage. Additionally, FIG. 3 shows that the expandable framework 12 may include a width depicted as "$Y_1$." Further, FIG. 3 shows that the expandable recess 21 (e.g., the recess defined by the support members 19) may include a depth depicted as "$Z_1$."

FIG. 4 illustrates the occlusive implant 10 after having shifted from the expanded configuration shown in FIG. 3 to a more collapsed configuration. In some examples, the occlusive implant 10 shown in FIG. 4 may represent the occlusive implant 10 illustrated and described above with respect to FIG. 2. It can further be appreciated from FIG. 4 that, as compared to the expanded implant shown in FIG. 3, the expandable framework 12 shown in FIG. 4 has been shifted to a narrower configuration as compared with the implant shown in FIG. 3. For example, FIG. 4 shows that the expandable framework 12 may include a width depicted as "$Y_2$." As discussed, the width $Y_2$ of FIG. 4 may be less than the width $Y_1$ of FIG. 3.

Additionally, while FIG. 4 shows the implant 10 having a narrower width (as compared to the implant shown in FIG. 3), FIG. 4 further illustrates that the "height" (defined as the distance between the proximal end region 11 and the distal end region 13) may remain substantially constant. For example, the height of the expandable framework 12 in FIG. 4 may remain as "X," which represents the same height of the expandable framework 12 illustrated in FIG. 3.

However, in order for the width of the expandable framework 12 to shift while maintaining a constant height, the plurality of support members 19 may curl (e.g., bend, flex, etc.) radially inward and upward toward the distal end region 13, thereby deepening the recess 21 within the expandable framework 12. For example, FIG. 4 shows the depth of the recess 21 depicted as "$Z_2$," whereby the distance $Z_2$ is greater than $Z_1$ shown in FIG. 3. Further, it can be appreciated from FIG. 4 that as the support members 19 curl radially inward and upward toward the distal end region 13 of the expandable framework 12, the hub member 23 may shift in a proximal-to-distal direction along the longitudinal axis 52.

FIG. 5 illustrates the occlusive implant 10 after having shifted from the configuration shown in FIG. 4 to an even narrower configuration. For example, as compared to the implant 10 shown in FIG. 4, the expandable framework 12 shown in FIG. 5 has been shifted to a collapsed configuration as compared with the implant shown in FIG. 4. For example, FIG. 5 shows that the expandable framework 12 may include a width depicted as "$Y_3$." As discussed, the width $Y_3$ of FIG. 5 may be less than the width $Y_1$ of FIG. 3 and $Y_2$ of FIG. 4.

As discussed above, while FIG. 5 shows the implant 10 having a narrower width (as compared to the implants shown in FIG. 3 and FIG. 4), FIG. 5 further illustrates that the "height" (defined as the distance between the proximal end region 11 and the distal end region 13) may remain substantially constant. For example, the height of the expandable framework 12 in FIG. 5 may remain as "X," which represents the same height of the expandable framework 12 as illustrated in FIG. 3 and FIG. 4.

Additionally, FIG. 5 illustrates that as the implant 10 continues narrows from an expanded configuration to a collapsed configuration, the plurality of support arms 19 may curl radially inward and upward toward the distal end region 13, thereby extending the recess 21 into the expandable framework 12. For example, FIG. 5 shows the depth of the recess 21 depicted as "$Z_3$," whereby the distance $Z_3$ is greater than $Z_1$ shown in FIG. 3 and $Z_2$ shown in FIG. 4. Further, it can be appreciated from FIG. 5 that as the support members 19 continue to curl radially inward and upward toward the distal end region 13 of the expandable framework 12, the hub member 23 may shift in a proximal-to-distal direction along the longitudinal axis 52.

As discussed above, in some instances it may be desirable to design implant 10 (or any other implants discussed herein) to maintain a substantially constant radial outward force independent of the particular configuration (e.g., geometry) the implant 10 may assume when positioned within left atrial appendages of different sizes and shapes. For example, it is contemplated that each of the configurations of the implant 10 illustrated in FIGS. 3-5 may exert a substantially equivalent outward radial force upon the walls of an atrial appendage. This design feature is present in the implant 10 because the "Z" dimension is the bending moment arm of the supporting members 19, and hence, because the "Z" dimension varies inversely with the device diameter, the device is able to maintain approximately constant radial force independent of its particular deployed geometry. For example, at low diameters the material strain is high, however, the bending moment is large. However, at high diameters the material strain is low, however, the bending moment is small. This feature gives rise to approximately constant outward radial force from the supporting members 19 throughout a range of configurations (e.g., a range of configurations illustrated in FIGS. 3-5).

Figure 6:
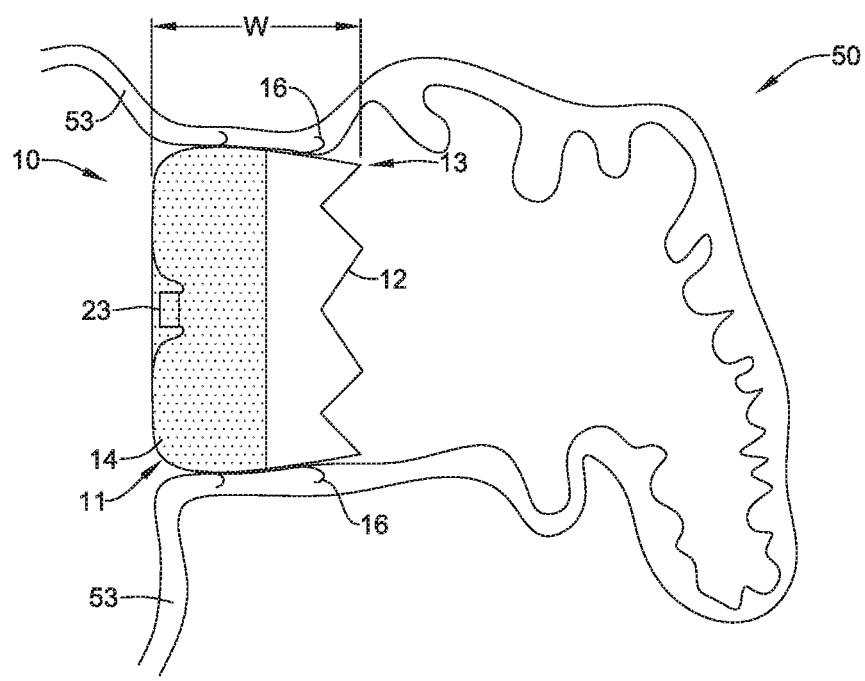
FIG. 6 illustrates an example occlusive implant positioned in the left atrial appendage.
Figure 7:
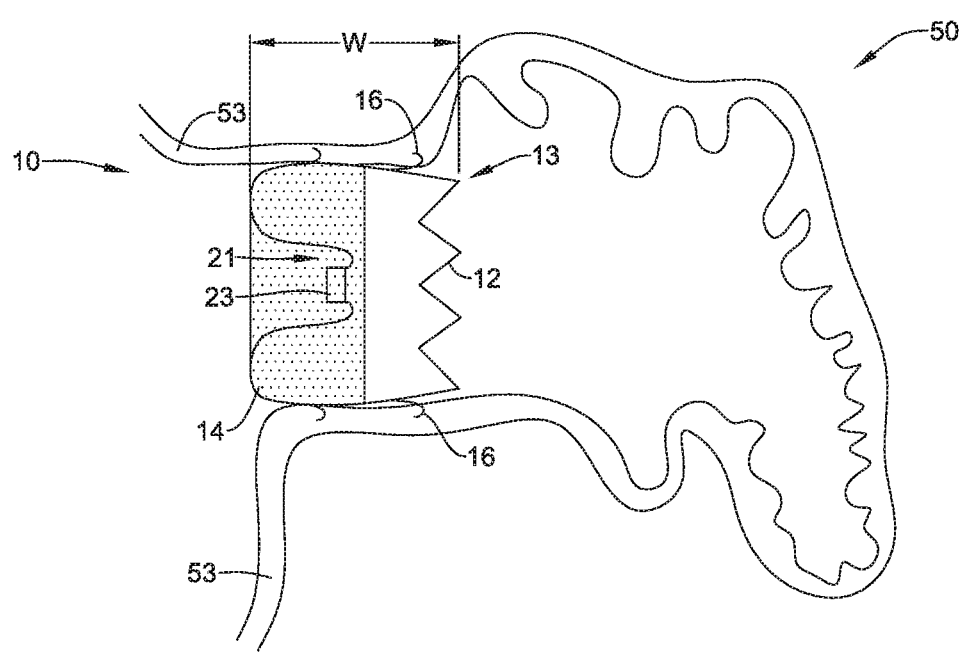
FIG. 7 illustrates another example occlusive implant positioned in the left atrial appendage.

FIG. 6 and FIG. 7 illustrates the occlusive implant 10 positioned within an example left atrial appendage 50. Further, FIG. 6 illustrates the implant 10 being positioned in a left atrial appendage having a wider orifice, while FIG. 7 illustrates the implant 10 being positioned in a left atrial appendage having a narrower orifice (as compared to FIG. 6).

As shown, FIG. 6 and FIG. 7 illustrate that the expandable framework 12 may be compliant and, therefore, substantially conform to and/or be in sealing engagement with the shape and/or geometry of a lateral wall 53 of a left atrial appendage 50. In some embodiments, the occlusive implant 10 may expand to a size, extent, or shape less than or different from a maximum unconstrained extent, as determined by the surrounding lateral wall 53 of the left atrial appendage. Additionally, FIG. 6 and FIG. 7 illustrate that the expandable framework 12 may be held fixed adjacent to the left atrial appendage by one or more anchoring members 16.

Additionally, FIG. 6 illustrates the occlusive implant 10 positioned within the opening to the left atrial appendage 50 such that it extends into the appendage a distance depicted as "W." Further, it can be appreciated from FIG. 6 that the opening to the left atrial appendage 50 shown in FIG. 6 may require that the occlusive member 10 expand to a wide configuration (similar to the configuration shown in FIG. 3). In this expanded configuration, the hub 23 is positioned adjacent to the proximal end region of the occlusive member 10.

As discussed above, FIG. 7 illustrates the occlusive implant 10 is positioned within a left atrial appendage 50 having narrower opening as compared to the left atrial appendage illustrated in FIG. 6. However, FIG. 7 further illustrates that even though the implant 10 is positioned within a left atrial appendage 50 having a narrower opening, the distance in which it extends into the left atrial appendage 50 remains substantially constant. In other words, even though the occlusive implant 10 deployed within a narrower orifice, the distance it extends into the left atrial appendage 50 remains "W." Further, it can be appreciated from FIG. 7 that the opening to the left atrial appendage 50 shown in FIG. 7 may require that the occlusive member collapse to a narrower configuration (similar to the configuration shown in FIG. 5). As discussed above, in this narrowed configuration, the plurality of support members (not shown in FIG. 7) may curl radially inward and upward toward the distal end region 13 such that the hub 23 extends within a deepened recess 21 of the expandable framework 12.

Figure 8:
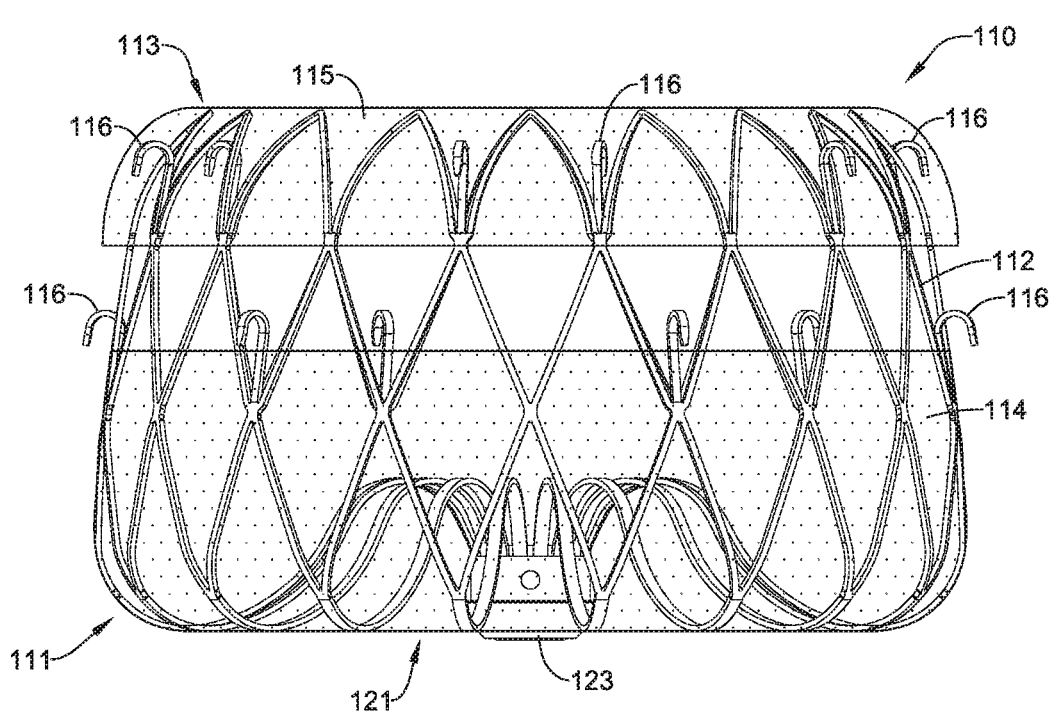
FIG. 8 is a plan view of an example occlusive implant.

FIG. 8 illustrates another example occlusive member 110. The occlusive member 110 may be similar in form and function to the occlusive member 10 described above. For example, the occlusive member 110 may include an expandable framework 112 and a first occlusive member 114 disposed along a proximal end region 111 of the expandable framework 112. Additionally, the expandable framework 112 may include a plurality of anchor members 116 disposed about a periphery of the expandable framework 112. The plurality of anchor members 116 may extend radially outward from the expandable framework 112. Some suitable, but non-limiting, examples of materials for the expandable framework 112 and/or the plurality of anchor members 116 are discussed below.

Further, FIG. 8 illustrates that the occlusive member 110 may include a second occlusive member 115 disposed along a distal end region 113 of the expandable framework 112. In some embodiments, the second occlusive member 115 may be disposed on, disposed over, disposed about or cover at least a portion of an outer (or outwardly-facing) surface of the expandable framework 112. FIG. 8 further illustrates that the second occlusive member 115 may extend only partially along the longitudinal extent of the expandable framework 112. However, this is not intended to be limiting. Rather, the second occlusive member 115 may extend along the longitudinal extent of the expandable framework 112 to any degree (e.g., the full longitudinal extend of the expandable framework 112).

In some embodiments, the second occlusive member 115 may be permeable or impermeable to blood and/or other fluids, such as water. In some embodiments, the second occlusive member 115 may include a woven, braided and/or knitted material, a fiber, a sheet-like material, a fabric, a polymeric membrane, a metallic or polymeric mesh, a porous filter-like material, or other suitable construction. In some embodiments, the second occlusive member 115 may prevent thrombi (i.e. blood clots, etc.) from passing through the second occlusive member 115 and out of the left atrial appendage into the blood stream. Some suitable, but non-limiting, examples of materials for the second occlusive member 115 are discussed below.

Figure 9:
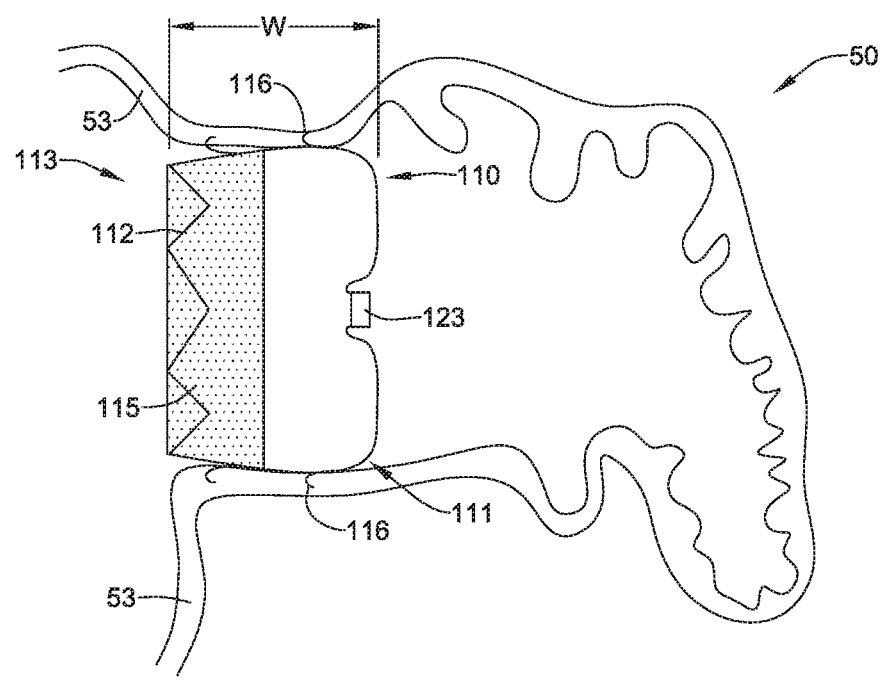
FIG. 9 illustrates an example occlusive implant positioned in the left atrial appendage.
Figure 10:
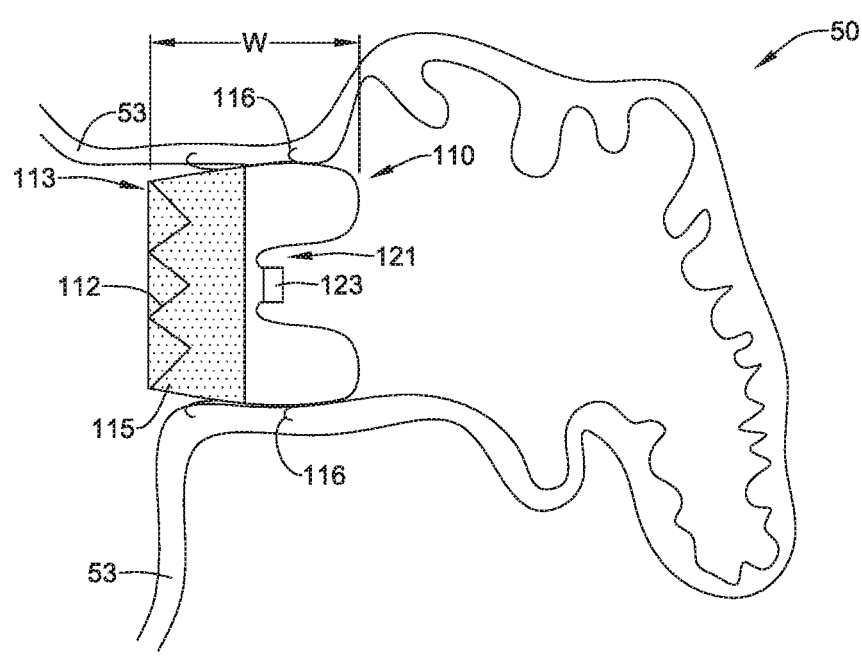
FIG. 10 illustrates another example occlusive implant positioned in the left atrial appendage.

Similar to FIG. 6 and FIG. 7 above, FIG. 9 and FIG. 10 illustrate the occlusive implant 110 positioned within an example left atrial appendage 50. For simplicity purposes, the implant 110 is shown with the second occlusive member 115 positioned on the distal end region 113, but omits the first occlusive member 114. However, it is contemplated that the implant 110 may include the first occlusive member 114, the second occlusive member 115 or both the first occlusive member 114 and the second occlusive member 115. Further, FIG. 9 illustrates the implant 10 being positioned in a left atrial appendage having a wider orifice, while FIG. 10 illustrates the implant 10 being positioned in a left atrial appendage having a narrower orifice (as compared to FIG. 9).

As shown, FIG. 9 and FIG. 10 illustrate that the expandable framework 112 may be compliant and, therefore, substantially conform to and/or be in sealing engagement with the shape and/or geometry of a lateral wall 53 of a left atrial appendage 50. In some embodiments, the occlusive implant 110 may expand to a size, extent, or shape less than or different from a maximum unconstrained extent, as determined by the surrounding lateral wall 53 of the left atrial appendage. Additionally, FIG. 9 and FIG. 10 illustrate that the expandable framework 112 may be held fixed adjacent to the left atrial appendage by one or more anchoring members 116.

Additionally, FIG. 9 illustrates the occlusive implant 110 positioned within the opening to the left atrial appendage 50 such that the proximal end region 111 extends into the appendage 50 a distance depicted as "W" and the distal end region 113 is positioned adjacent to the opening of the left atrial appendage. Further, it can be appreciated from FIG. 9 that the opening to the left atrial appendage 50 shown in FIG. 9 may require that the occlusive member 110 expand to a wide configuration. In this expanded configuration, the hub 123 is positioned adjacent to the proximal end region 111 of the occlusive member 10.

As discussed above, FIG. 10 illustrates the occlusive implant 110 is positioned within a left atrial appendage 50 having narrower opening as compared to the left atrial appendage illustrated in FIG. 9. However, FIG. 10 further illustrates that even though the implant 110 is positioned within a left atrial appendage 50 having a narrower opening, the distance in which it extends into the left atrial appendage 50 remains substantially constant. In other words, even though the occlusive implant 110 is deployed within a narrower orifice, the distance it extends into the left atrial appendage 50 remains "W." Further, it can be appreciated from FIG. 10 that the opening to the left atrial appendage 50 shown in FIG. 10 may require that the occlusive member collapse to a narrower configuration. As discussed above, in this narrowed configuration, the plurality of support members (not shown in FIG. 10) may curl radially inward and upward toward the distal end region 113 such that the hub 123 extends within a deepened recess 121 of the expandable framework 112.

Figure 11:
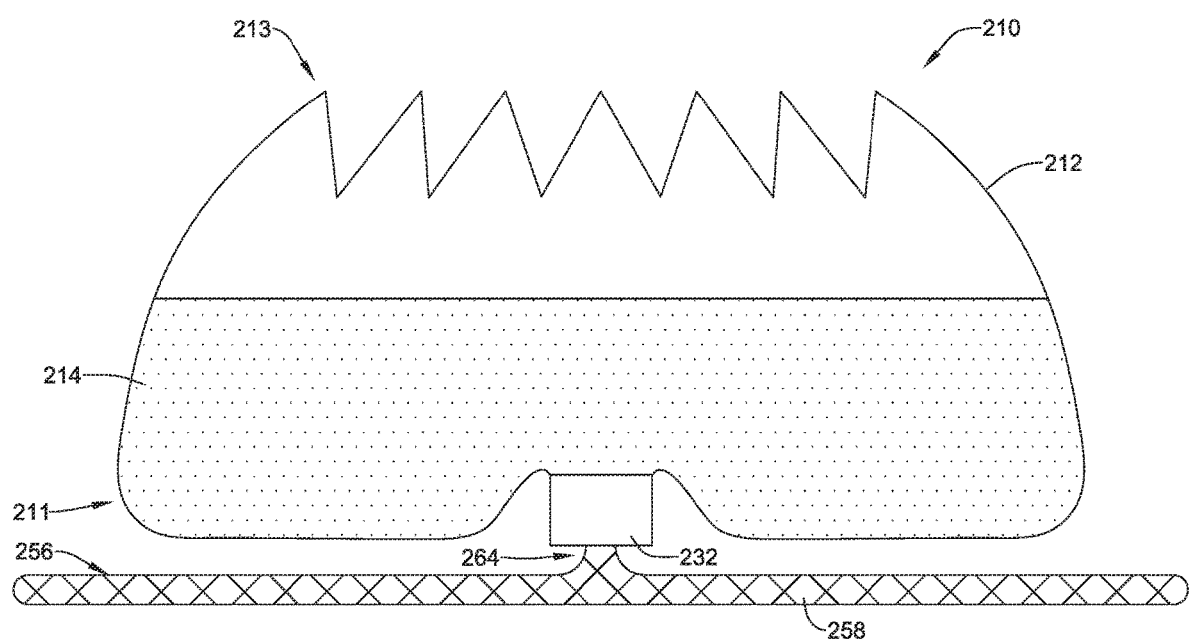
FIG. 11 is a plan view of another example occlusive implant.

FIG. 11 illustrates another example occlusive member 210. It can be appreciated that FIG. 11 illustrates the occlusive member 210 in an expanded configuration. The occlusive member 210 may be similar in form and function to the occlusive member 10 described above. For example, the occlusive member 210 may include an expandable framework 212 and an occlusive member 214 disposed along a proximal end region 211 of the expandable framework 212. Additionally, FIG. 11 illustrates that the occlusive member 210 may include an occlusive disk 256 positioned adjacent to the proximal end region 211 of the occlusive member 210. In some embodiments, the occlusive disk 256 may include a woven, braided and/or knitted material, a fiber, a sheet-like material, a fabric, a polymeric membrane, a metallic or polymeric mesh, a porous filter-like material, or other suitable construction. Additionally, FIG. 11 illustrates that the occlusive disk 256 may include an attachment region 264 which is coupled to the hub member 232 of the occlusive implant 210.

Figure 12:
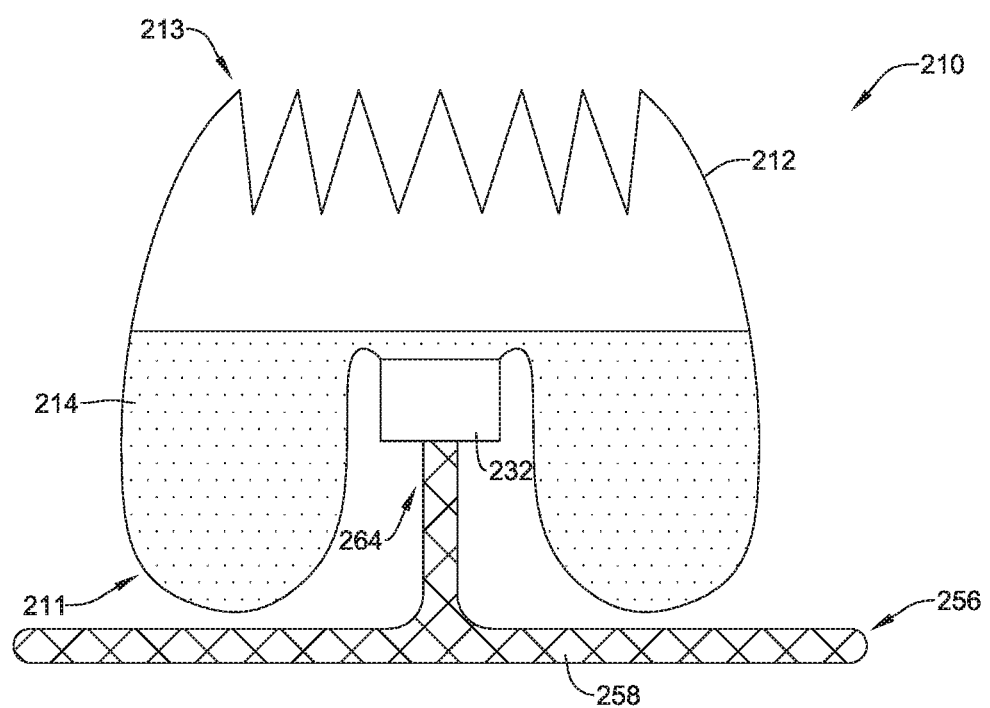
FIG. 12 is a plan view of the occlusive implant of FIG. 11 in a collapsed configuration.

FIG. 12 illustrates the occlusive member shown in FIG. 11 in a collapsed (e.g., narrowed) configuration. As can be appreciated from FIG. 12, the occlusive disk 256 (described above) may narrow as the occlusive member 210 narrows. Further, it can be appreciated that the attachment region 264 of the occlusive disk 256 may extend into the recess of the expandable member 212. In other words, as the support members (not shown in FIG. 12 but described above) of the expandable framework 212 curl radially inward and upward toward the distal end region 213, the attachment region 264 may be "pulled" by the hub member 232 up into the recess within the expandable member. Accordingly, as the attachment region 264 is pulled into the recess, the occlusive disk 256 member may narrow while remaining positioned adjacent to the proximal end region 211.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, TINS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an Mill image. The occlusive implant 10 (and variations, systems or components disclosed herein) or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:
   an expandable framework including a height and a plurality of support members defining a proximal end region of the expandable framework;
   a first occlusive member disposed along the proximal end region of the expandable framework;
   a central hub member attached to the plurality of support members;
   an occlusive disk positioned proximal of the proximal end region, the occlusive disk including an attachment region coupled to the central hub member;
   wherein the expandable framework is configured to shift between a first configuration and a second configuration, wherein the height of the expandable framework remains substantially the same in both the first configuration and the second configuration;
   wherein the central hub member is configured to shift relative to the proximal end region while the expandable framework shifts between the first configuration and the second configuration; and
   wherein the occlusive disk is configured to remain proximal of the proximal end region of the expandable framework in both the first configuration and the second configuration.

2. The occlusive implant of claim 1, wherein the expandable framework includes a first radial outward force in the first configuration and a second radial outward force in the second configuration, and wherein the first radial outward force is substantially equivalent to the second radial outward force.

3. The occlusive implant of claim 1, wherein the expandable framework includes a longitudinal axis, and wherein the central hub member is configured to shift along the longitudinal axis.

4. The occlusive implant of claim 1, wherein the central hub member shifts in a distal direction when shifting from the first configuration to the second configuration.

5. The occlusive implant of claim 1, wherein the plurality of support members defines a recess within a central region of the expandable framework.

6. The occlusive implant of claim 5, wherein the central hub member is positioned within the recess.

7. The occlusive implant of claim 6, wherein the expandable framework has a first width in the first configuration and a second width in the second configuration, wherein the first width is wider than the second width.

8. The occlusive implant of claim 5, wherein the recess of the expandable framework has a first recess height in the first configuration and a second recess height in the second configuration, and wherein the second recess height is greater than the first recess height; wherein in the second configuration, the attachment region of the occlusive disk elongates within the recess and the occlusive disk narrows.

9. The occlusive implant of claim 1, further comprising a second occlusive member disposed along a distal end region of the expandable framework.

10. A medical implant adapted to occlude a left atrial appendage, comprising:
    an expandable framework including a first height, a proximal end region and a plurality of support members defining a central recessed region;
    a first occlusive member disposed along the proximal end region of the expandable framework;

a central hub member attached to the plurality of support members and positioned within the central recessed region; and an occlusive disk positioned proximal of the proximal end region, the occlusive disk including an attachment region coupled to the central hub member;

wherein the central recessed region extends into the expandable framework a first distance;

wherein the expandable framework is configured to shift between an expanded configuration and a collapsed configuration;

wherein the first height of the expandable framework remains substantially the same in both the expanded configuration and the collapsed configuration;

wherein the first distance increases as the expandable framework shifts between the expanded configuration and the collapsed configuration;

wherein the occlusive disk is configured to remain proximal of the proximal end region of the expandable framework in both the expanded configuration and the collapsed configuration.

11. The medical implant of claim 10, wherein the expandable framework includes a first radial outward force in the expanded configuration and a second radial outward force in the collapsed configuration, and wherein the first radial outward force is substantially equivalent to the second radial outward force.

12. The medical implant of claim 11, wherein the central hub member is configured to shift relative to the proximal end region while the expandable framework shifts between the expanded configuration and the collapsed configuration.

13. The medical implant of claim 12, wherein the expandable framework includes a longitudinal axis, and wherein the central hub member is configured to shift along the longitudinal axis.

14. The medical implant of claim 10, wherein the central hub member shifts in a distal direction when shifting from the expanded configuration to the collapsed configuration.

15. The medical implant of claim 10, further comprising a second occlusive member disposed along a distal end region of the expandable framework.

* * * * *